US007962544B2

(12) United States Patent
Torok et al.

(10) Patent No.: US 7,962,544 B2
(45) Date of Patent: Jun. 14, 2011

(54) PATIENT AND DEVICE LOCATION DEPENDENT HEALTHCARE INFORMATION PROCESSING SYSTEM

(75) Inventors: David Torok, Philadelphia, PA (US); Jeffrey Gardiner, Phoenixville, PA (US); Domonic Snyder, Whitehall, PA (US); Christopher Gardner, Charlotte, NC (US); William Boggs, Acworth, GA (US); Robert D. Williamson, Columbus, OH (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 991 days.

(21) Appl. No.: 11/407,529

(22) Filed: Apr. 20, 2006

(65) Prior Publication Data
US 2006/0288095 A1   Dec. 21, 2006

Related U.S. Application Data (63) Continuation-in-part of application No. 10/852,885, filed on May 25, 2004, now abandoned.

(60) Provisional application No. 60/676,728, filed on May 2, 2005.

(51) Int. Cl.
G06F 15/16        (2006.01)
(52) U.S. Cl. .......................................... 709/200; 705/3
(58) Field of Classification Search .................. 709/203, 709/200; 705/3
See application file for complete search history.

(56) References Cited

U.S. PATENT DOCUMENTS

| 5,581,753 | A | 12/1996 | Terry et al. |
| 6,058,381 | A | 5/2000 | Nelson |
| 6,349,337 | B1 * | 2/2002 | Parsons et al. ............... 709/227 |
| 6,477,487 | B1 | 11/2002 | Packer |
| 6,775,588 | B1 * | 8/2004 | Peck ............................. 700/214 |
| 2002/0065912 | A1 | 5/2002 | Catchpole et al. |
| 2002/0183979 | A1 * | 12/2002 | Wildman ...................... 702/188 |
| 2003/0001009 | A1 * | 1/2003 | Collins et al. ................. 235/385 |

(Continued)

OTHER PUBLICATIONS

Cheng-Ju Li; Li Liu; Shi-Zong Chen; Chi Chen Wu; Chun-Huang Huang; Xin-Mei Chen; , "Mobile healthcare service system using RFID," Networking, Sensing and Control, 2004 IEEE International Conference on , vol. 2, No., pp. 1014-1019 vol. 2, 2004.*

(Continued)

*Primary Examiner* — Ajay Bhatia
(74) *Attorney, Agent, or Firm* — Alexander J Burke (57) ABSTRACT

A system automatically establishes context information (e.g., determining changes to user interface workflows, screens, menus, and access requirements for devices such as monitors, ventilators, and diagnostic equipment) used by a worker in using healthcare information applications based on patient geographic location (e.g., a room or bed or department). The system addresses the need for a user to sign onto a system with each location change and manually change context information which consumes computer, server and network resources and represent a potential security problem. A healthcare system selects information to be provided to a user in response to received location dependent context data. The system includes a proximity detector for wirelessly detecting presence of an identification tag substantially within a predetermined vicinity of the detector. The identification tag is associated with at least one of, (a) a particular processing device and (b) a particular person. A location detector determines location information indicating a location associated with an identification tag detected by the proximity detector. A workflow processor automatically alters information presented to a user including information associated with a task sequence to be performed by the user for a patient in response to the determined location information.

33 Claims, 5 Drawing Sheets

U.S. PATENT DOCUMENTS

| | | |
|---|---|---|
| 2003/0187991 A1 | 10/2003 | Lin et al. |
| 2004/0193449 A1* | 9/2004 | Wildman et al. ................. 705/2 |
| 2005/0035862 A1* | 2/2005 | Wildman et al. .......... 340/573.1 |
| 2005/0114177 A1* | 5/2005 | Sweeney ........................... 705/2 |
| 2006/0036472 A1* | 2/2006 | Crockett ........................... 705/3 |
| 2006/0074519 A1* | 4/2006 | Barker et al. ................. 700/213 |
| 2006/0200369 A1* | 9/2006 | Batch et al. ...................... 705/3 |
| 2008/0294692 A1* | 11/2008 | Angell et al. ............. 707/104.1 |

OTHER PUBLICATIONS

Foster, K.R.; Jaeger, J.; , "RFID Inside," Spectrum, IEEE , vol. 44, No. 3, pp. 24-29, Mar. 2007.*

U.S. Appl. No. 60/676,728, filed May 2, 2005, Torok.

U.S. Appl. No. 10/852,885, filed May 12, 2005, Gardiner.

* cited by examiner

# PATIENT AND DEVICE LOCATION DEPENDENT HEALTHCARE INFORMATION PROCESSING SYSTEM

This is a non-provisional application based on provisional application Ser. No. 60/676,728 by J. Gardiner filed May 2, 2005 and comprising a Continuation In Part Application of application Ser. No. 10/852,885 filed by J. Gardiner May 25, 2004 now abandoned.

FIELD OF THE INVENTION

This invention concerns a system for selecting information to be provided to a user in response to received patient and device location dependent context data.

BACKGROUND OF THE INVENTION

Although existing systems identify the assignment of patients or equipment to rooms, these systems are typically not sensitive to user physical (geographic) location. Such systems are not sensitive to user geographic location in navigating through user interfaces, selecting patients or locations from a list, or signing off at an old location and re-entering password information at a new location, for example. In existing systems a user manually chooses context, such as selecting a patient from a list of many patients, including patients not present at the user's location. A user is required to sign-off from an old location and to re-enter password information at a new location and then manually select context (e.g., user identifier or patient identifier). The need for a user to sign onto a system with each location change and manually change context information creates user dissatisfaction and increases risk of error due to context information selection and data entry.

A user may connect to different applications executing on the same or different servers from one or more workstations at different locations. If a user roams from one location to another without properly disconnecting a session of operation, the session remains "active". In existing systems, when a user connects to a server from a new location, a new session is created even though there is a concurrent previously created operation session. The reason for this is that the previously created session is in an "active" rather than "disconnected" state. Therefore there are two "active" sessions associated with the user. If this goes on repeatedly a user will create many concurrent "active" sessions of computer operation. This is undesirable because multiple sessions consume computer, server and network resources and represent a potential security problem. Also, a user that initiates a second concurrent session may need to engage in burdensome navigation to return to a previous position achieved in a first session to continue work tasks using an application. A system according to invention principles addresses these problems and related problems.

SUMMARY OF THE INVENTION

A system automatically establishes context information (e.g., determining changes to user interface workflows, screens, menus, and access requirements for devices such as monitors, ventilators, and diagnostic equipment) used by a worker in using healthcare information applications based on patient geographic location (e.g., a room or bed or department). The system addresses the need for a user to sign onto a system with each location change and manually change context information which consumes computer, server and network resources and represent a potential security problem. A healthcare system selects information to be provided to a user in response to received location dependent context data. The system includes a proximity detector for wirelessly detecting presence of an identification tag substantially within a predetermined vicinity of the detector. The identification tag is associated with at least one of, (a) a particular processing device and (b) a particular person. A location detector determines location information indicating a location associated with an identification tag detected by the proximity detector. A workflow processor automatically alters information presented to a user including information associated with a task sequence to be performed by the user for a patient in response to the determined location information.

DETAILED DESCRIPTION OF INVENTION

A system updates displayed User Interface data (e.g., workflows and menus) based on automatically determined context information. The context information is derived from workstation geographic location data, patient and healthcare worker geographic location data (such as room or bed or department, acquired using wireless identification tags) and current task sequence workflow status information of a user or patient. The context information enables automatic changes to User Interface menus as well as selected workflows and enables enhancements and alterations to User Interface operation and displayed windows based on user or patient location alone or in combination with logged-in user identification data. The wireless location data is obtained using RFID, WIFI, GPS, wired plug location, or a device address, for example. The system is usable by workstations including a mobile laptop, a tablet computer, PDA, or desktop PC in a fixed or mobile cart configuration. The determined context information enables automatic acquisition and presentation and access to items such as, patient lists and related demographic data, test or laboratory Equipment (such as EKG, EEG equipment), Test or Laboratory Equipment monitors, ventilators, and diagnostic and results, healthcare workers and related data, for example.

Figure 1:
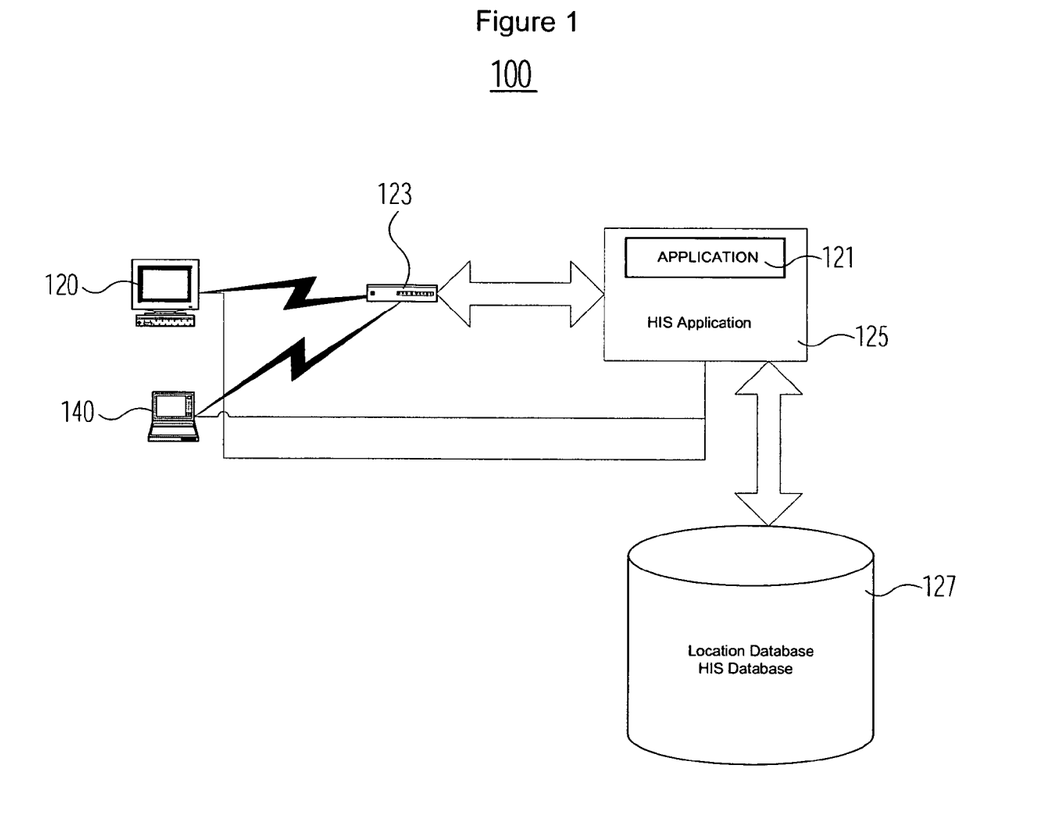
FIG. 1 shows a block diagram of a system for determining changes in information presented in user interface workflows, screens, menus, and access requirements for devices provided to a user in response to received location dependent context data, according to invention principles.

FIG. 1 shows a block diagram of system 100 for determining information and information changes presented in user interface workflows, screens, menus, and access requirements for devices provided to a user in response to received location dependent context data. System 100 involves a Hospital Information System (HIS) or Clinical Information System (CIS), for example, in automatically registering a device location and associating a patient in a predetermined proximity to a particular device. This enables system 100 to present a user with patient active case information compatible with user context information and with their allowable workflow menus. In system 100, executable application 121 in HIS 125 determines geographic location of mobile processing device (or patient or worker or medical equipment) 140 and fixed location processing device 120 using wireless location data acquired by tag reader device 123. For this purpose, wireless location data provided by Active or Passive RFID (Radio Frequency Identification) tags is acquired by tag reader device 123, for example. In alternative embodiments, application 121 determines geographic location of mobile processing device (or patient or worker) 140 and fixed location processing device 120 using wireless location data acquired via a wireless network connection (e.g., "WiFi" connection point) or based on wired plug location and computer identification such as Ethernet or MAC address in conjunction with a predetermined map associating a wired plug location or address with a geographic location. Application 121 determines geographic location of mobile item 140 or fixed item 120 in response to user action or selection when interacting with HIS 125.

Application 121 processes geographic location data of items 120 and 140 and information identifying events indicating geographic location change and associates geographic location specific data with a corresponding user session of computer operation using database 127. In another embodiment database 127 may comprise multiple centralized or distributed repositories. System 100 includes a user interface application in application 121 or within an application in a client device (e.g., device 120 or 140) or in a device anywhere else in the network. The user interface application adapts user context information including user interface workflows, screens, menus, and access requirements for devices accessible by a user in response to received changed location specific data associated with a user session. Database 127 is a repository of HIS clinical information as well as wirelessly acquired geographic location data of items 120 and 140 and information associating patients with geographic location. Information in database 127 also associates assets and medical equipment with geographic locations and associates workstation identifiers with corresponding workstation geographic present location. The geographic location information is derived by RFID tag reader device 123 or by network administrator assignment and data entry, for example. System 100 advantageously seamlessly presents relevant patient information to a user (excluding information from patients not concerned) without requiring a user to sign onto a new workstation at a different geographic location and reduces queuing for a workstation to become available. System 100 provides more efficient use of hardware resources and reduces need for processing and interfacing resources and facilitates workload sharing by mobile processing devices without involving rewiring of a facility.

In automatic operation of system 100, a healthcare worker currently logged onto workstation 140 in a first location is responsible for the care of a patient census list of thirty patients and initiates a workflow (a sequence of tasks for performance by device or personnel) comprising reviewing patient test results. The healthcare worker moves (with workstation 140) to a second location, specifically a bed room containing two patients. A Location Sensing Device (such as RFID tag Reader 123) identifies workstation 140 as being in the bed room. RFID tag reader 123 sends geographic location identification and workstation identification information to a central Current Location Server application, e.g., server based application 121 in HIS 125. Application 121 automatically receives the geographic location identification and workstation identification information and initiates communication of a patient identification query message to database 127. Application 121 receives return message data identifying the first and second patients in the bed room. In response to the identification and workstation identification information, application 121 also initiates communication of a medical equipment query message to database 127 and receives return message data identifying that a cardiac monitor is located in the bedroom.

Application 121 uses database 127 to automatically associate working context information of the healthcare worker currently logged onto workstation 140 with the first and second patients in the bed room. The working context information comprises user identifier and application specific context information such as patient identifier and patient or user specific commands and data access requests such as a command to review patient test results. Consequently, application 121 automatically associates the (new) bed room second location with the first and second identified patients and cardiac monitor and working context information using database 127 that previously existed in the first location. The user interface display images presented on workstation 140 are automatically updated to display information concerning the identified first and second patients. In a further embodiment, the user interface display images presented on workstation 140 are updated to display information concerning the identified first and second patients exclusive of information of other patients. In response to the healthcare worker currently logged onto workstation 140 electing to review medical data of the first or second patient, the medical data and test results of the selected first or second patient is displayed on workstation 140. The User Interface displays the patient results and also the data from the automatically associated Cardiac Monitor which is in the bed room of the first and second patients and monitoring the selected first or second patient.

System 100 automatically provides healthcare worker role-based user workflow data that changes based on who is logged in and the location of the worker and associated patients. System 100 automatically determines healthcare worker role and initiates login and session transfer of a user based on worker geographic location identification information (automatically determined from RFID tag tracking, for example) as a user moves from workstation to workstation. System 100 automatically initiates transfer of a computer operation session to follow a user to a new location and new workstation (based on user RFID tag detection, for example via reader 123). Wireless tag reader 123 detects location of a moving workstation (e.g., mobile processing device 140) and an RFID on the workstation (such as a cart mounted workstation) is thereby aware of where it is and automatically employs a workflow task sequence appropriate for the location as well as the user role and the function the user is engaged in. In an example, a user such as a physician is visiting patients in a hospital (doing the rounds) and carries a laptop computer from room to room. System 100 automatically updates workflow task sequences and associated information in response to the identification of patients in the room determined from user location data and/or workstation location data.

A user interface in system 100 provides functions and workflow menus in response to a combination of user location and user role and location based workflow (e.g., functions available in an operating room (O.R.) that are different than functions available in a patient room). The user interface provides a user with information available based on personnel and resources available at a location (such as patients, medical equipment). A physician is presented with information concerning two patients occupying a particular room, for example, rather than information concerning the fifty patients on a patient list for whom the physician is responsible. Further, the system 100 user interface automatically provides information associated with particular medical equipment (such as a patient parameter results chart) in response to a determination that particular medical equipment is in the location of the user. The automatic location and role dependent user interface adaptability features of system 100 advantageously support and facilitate a combination of bed management, asset management and workflow update.

System 100 workflow directed task sequences (including functions allowed to be performed and workflow available) and associated user interface images are adapted based on whether (a) personnel or (b) equipment, is detected as having moved. A next step in a healthcare worker workflow is selected, for example, based on type of work being performed at a location which is automatically predicted based on identity of healthcare workers, patient and type of equipment at a location. As a user is moving from room to room a roaming user session of computer operation follows the user and system 100 automatically logs the user in to a workstation in the vicinity of the user at a detected new location determined from RFID tag detection. Further, functions available on the workstation are adapted based on the role of the user. In the event that a workstation is moving from room to room, system 100 workflow directed task sequences and associated user interface images are adapted to provide functions available based on the nature (or other attribute) of a location (e.g., whether the location is an operating room, examination room, radiology department or patient room, for example).

System 100 workflow directed task sequences, as well as functions available on the workstation, are also adapted and information displayed in associated user interface images is adapted, based on the type of medical equipment and the identity of patients in a user location as well as the information available (e.g. the patients for whom a particular physician is responsible). The RFID tag reader device 123 detects location of medical equipment and other mobile resources and tracks movement of the medical equipment and other mobile resources between rooms. System 100 adapts information (e.g., charts, vital signs) displayed on a workstation based on the detected type and location of medical equipment (and other assets). Similarly, the RFID tag reader device 123 detects location of patients and tracks movement of patients between rooms and system 100 adapts patient information displayed on a workstation based on the detected identity of patients at a location.

In an example of operation, a nurse is making rounds with a workstation and enters a patient room having two beds. Application 121 operating in conjunction with tag reader device 123 determines that a nurse is nearby and logs in on the workstation. The nurse is responsible for the care of thirty patients, but the workstation, employing the location information provided by device 123 and application 121, automatically provides a patient information dialog on the workstation user interface showing the specific two patients in the room (and excluding other patients) to select from. The nurse selects a particular one of the two patients and application 121 initiates presentation on the workstation of a chart for the selected particular patient derived from a cardiac monitor in the room. The nurse completes the assessment, performs a similar assessment on the second patient assigned to the room and finishes the rounds and returns to the nurse station. The workstation shows the next step in the rounds workflow comprising prompting a user to initiate printing of a rounds assessment report. The report is automatically printed to the printer at the same nurse station.

Figure 2:
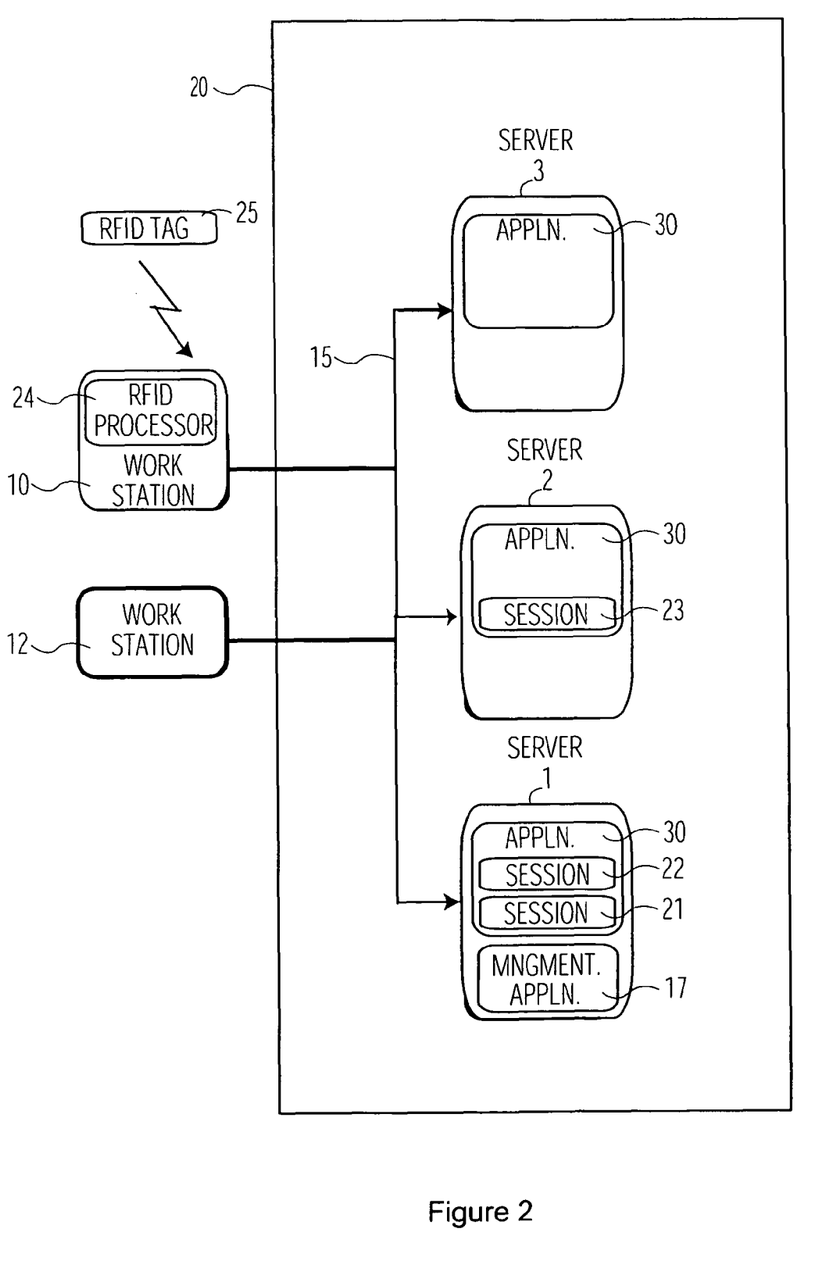
FIG. 2 shows a block diagram of a system for managing user operation sessions on one or more different servers, according to invention principles.

FIG. 2 shows a block diagram of a system for managing user operation sessions on one or more different servers. A session of operation, as used herein, includes a session of operation of an executable application or procedure or a session of operation of a processing device such as a workstation, PC, server, microprocessor, controller or portable processing device. As used herein, a "disconnected session" is an "orphaned" session having no client work stations connected with the session and an "active session" is a user session that does have a client work station connected with the session. Existing systems fail to comprehensively address session management in an environment in which a user creates a new session and has a previously created "active session". One known system reconnects a current user workstation to a previous "disconnected session" if a user logs on and connects to a server and a previously disconnected session initiated by the user exists. However, known systems fail to manage reconnection in the event that a user has a previous "active session" of operation. A system, according to invention principles, manages user operation sessions on a plurality of servers and enables users of a server (such as Citrix's current MetaFrame products (v1.8 and XP), for example) to seize a session that is actively connected to another device and attach it to a different device.

The system allows a user (such as a physician or another) to roam from one location to another (home to office; patient room to patient room; etc.) and have an active session follow the user, for example. The session returns to a position in an application (such as a particular displayed image) where a user left off at a previous location. The system addresses the situation where a user creates and abandons one or more active sessions throughout the course of a day, for example. The system advantageously reduces server overhead with roaming users by eliminating multiple sessions per user and improves security by eliminating abandoned sessions. The system also advantageously eliminates the need for a user to reestablish a session from scratch when an active session already exists elsewhere in a group of servers, for example.

An executable application as used herein comprises code or machine readable instruction for implementing predetermined functions including those of an operating system, healthcare information system or other information processing system, for example, in response to user command or input. A processor as used herein is a device and/or set of machine-readable instructions for performing tasks. As used herein, a processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A workstation comprises a terminal, display, PC, portable processing device or phone, for example and a server as used herein comprises a processing device, PC, laptop, notebook, PDA (Personal Digital Assistant, phone or other device.

In the FIG. 2 system, workstations 10 and 12 (e.g., corresponding to workstations 120 and 140 of FIG. 1) bidirectionally communicate on network 15 with a group of servers 20 (e.g., a Citrix compatible, or other server farm) including servers 1, 2 and 3. A user establishes a first (Primary) session of operation 21 of executable application 30 on server 1 of group of servers 20 following logon and entry of user identification information via workstation 10 and authentication of the entered user identification information. This first session 21 is a Primary session of operation meaning the first session established by the user on server group 20. A Primary session is a semi-permanent session that is dragged from workstation to workstation as the user roams around a hospital or office, for example. Subsequently, a user starts to initiate a second (Attached) session of operation of executable application 30 via workstation 12. An Attached session is one currently displayed on a user's workstation. The Primary and Attached sessions may or may not be the same session. An executable procedure (such as a Script) is executed on server 1 (or another server or on a workstation in another embodiment) to advantageously make Primary and Attached sessions of operation one and the same sessions if they are initially different separate sessions. That is, if the session Attached to a user's workstation is not the Primary session of operation, an executable application 17 procedure is executed on server 1 to make them a single Primary session of operation and to eliminate other sessions. Individual servers of group 20 include an interface for bidirectionally communicating with workstations 10 and 12 and for receiving requests to initiate a current session of operation of a particular executable application as well as for receiving user identification information from a particular user.

A user that logs on to initiate a session of operation on a server of server group 20 for a first time and for which no orphaned sessions (active or disconnected) exist anywhere in group 20, initiates execution of a script procedure which creates a Primary session of operation of an executable application on the server connected to the current user workstation. Application 17 enables a session to follow the user as the user roams from PC to PC whilst supporting load balancing among the servers of group 20 to distribute user load relatively evenly across the servers of group 20. A user that logs on and re-connects to server group 20 and for which an existing Primary session in a disconnected state exists on one of the servers of group 20, initiates re-connection of a current workstation to the server running the previous disconnected session.

In one scenario, a second (Attached) session of operation of executable application 30 on server 1 that is initiated by the user via workstation 12, coincidentally re-connects to server 1 of server group 20. Therefore both the first (Primary) session of operation 21 of executable application 30 which is still active and the second (Attached) session of operation 22 of application 30 of the user, are connected to the same server (server 1). Session management application 17 including a script procedure (e.g., a session processor compatible with a Citrix server product or other proprietary server management system, for example) executes on server 1 (or another server or on a workstation in another embodiment). The script procedure of application 17 executes in response to user logon to initiate a session of operation of application 30 and entry of user identification information via a workstation.

The script procedure of application 17 makes Primary and Attached sessions of operation one and the same sessions if they are initially different separate sessions. Specifically, in response to the user's second login via workstation 12, the application 17 script procedure initiates a search of session tracking information maintained on server 1. The search identifies the active first (Primary) session of operation 21 of executable application 30 on server 1 that was previously initiated via workstation 10 and is associated with the user.

The search of session tracking information maintained on server 1 is performed in response to received user identification information. The session tracking information is maintained on server 1 for the servers of group 20 and indicates active and disconnected sessions for different users and different applications for sessions of operation supported by the servers of group 20.

In another embodiment, the session tracking information may be maintained in another server of group 20 in a central repository or within multiple locations (e.g., by individual servers of group 20) or in another processing device such as a workstation connected to network 15. In a further embodiment, the application 17 script procedure may acquire session tracking information by deriving and compiling session tracking information from session associated status information acquired from one or more session manager applications (such as application 17) employed by server group 20. The status information indicates operation sessions still present on an individual server and is acquired by interrogating session operation history information retained by an individual server, for example. A session manager application manages opening of sessions and generation of unique session identifiers and associated user authentication operations for individual sessions supported by servers of group 20.

The application 17 script procedure identifies the active first (Primary) session of operation 21 of executable application 30 on server 1 that was previously initiated by the user via a workstation 10. This is done through search of session tracking information maintained on server 1 indicating operation sessions still present on server 1 that are associated with the previously entered user identification. The application 17 script procedure detaches the connection between workstation 10 and the active first (Primary) session of operation 21 of application 30 on server 1 by one or more of, disabling a communication link, disabling an association or mapping supporting communication and disabling a link supporting communication.

The application 17 script procedure re-attaches the connection of the detached active first (Primary) session of operation 21 to workstation 12 as the current second (Attached) session of operation 22 of executable application 30 without requiring re-authentication of received user identification information. In one Citrix server management system compatible embodiment, the application 17 script procedure automatically initiates a Citrix server pass-through client on the server running the current second (Attached) session 22. The Citrix server pass-through client re-attaches the connection of the detached active first (Primary) session of operation to workstation 12 as the current second (Attached) session without requiring a user to re-authenticate during the second connection. The re-attached session of operation continues at a position in an executable application comprising the active first (Primary) session of operation 21 where the user discontinued using this executable application. The application 17 script procedure re-attaches the connection by one or more of, enabling a communication link, establishing an association or mapping supporting communication and establishing a link supporting communication. The application 17 script procedure terminates sessions of operation on server 1 that are associated with the user, other than the re-attached detached active first (Primary) session of operation.

A user wearing RFID tag 25 (or another wireless technology identification tag or device) and roaming within a predetermined distance of workstation 10 (four feet, for example) activates an RFID sensor in RFID processor 24 (e.g., corresponding to detector 123 of FIG. 1) in workstation 10. The RFID tag conveys user identification information, or information enabling derivation of user identification, to RFID processor 24. Thereby, RFID processor 24 enables a user to automatically log-on to workstation 10 without entering a password or userid in response to proximity detection by workstation 10. The RFID tag may itself incorporate, in one embodiment, a biometric sensor so that it is activatable by a particular user. In response to detection of RFID tag 25 within a predetermined distance of workstation 10, RFID processor 24 using workstation 10 and application 17, automatically initiates transfer of a user Primary (active or disconnected) session involving one or more executable applications from another workstation at a different location to workstation 10 ready for access by the user. For this purpose workstation 10 includes an interface for generating a request message for communication to a remote server (e.g., server 1) for initiating a current session of operation of a particular executable application on workstation 10 (a processing device) by transferring an identified session of operation of the user previously initiated via workstation 12 to workstation 10 as the current session of operation. A processing device as used herein comprises a workstation, PC, laptop, notebook, PDA (Personal Digital Assistant, phone or other device. When the user leaves the predetermined vicinity of workstation 10 application 17 suspends and secures the initiated session ready for re-activation or movement to another workstation and location.

In a further scenario, a user establishes a first (Primary) session of operation 21 of executable application 30 on server 1 of group of servers 20 following logon and entry of user identification information via workstation 10 and authentication of the entered user identification information. Another (Attached) session of operation of executable application (session 23) on server 2 of server group 20 is initiated by the user via workstation 12. The first (Primary) session of operation 21 of executable application 30 which is still active and (Attached) session 23 of operation of application 30 of the user, are connected to different servers, server 1 and server 2 respectively. In response to the user's second login via workstation 12, the application 17 script procedure initiates a search of session tracking information for the servers of group 20 maintained on server 1 (or on another server or distributed among the servers of group 20).

The application 17 script procedure search identifies the active first (Primary) session of operation 21 of executable application 30 on server 1 associated with the user that was previously initiated by the user via workstation 10. The search comprises a search of session tracking information maintained on server 1. The application 17 script procedure detaches the connection between workstation 10 and the active first (Primary) session of operation 21 of application 30 on server 1 and re-attaches the connection of the detached active first (Primary) session of operation to workstation 12 as the current second (Attached) session of operation 23 of executable application 30. The application 17 script procedure terminates sessions of operation that are associated with the user and are present on servers of group 20, other than the re-attached detached active first (Primary) session of operation. The system of FIG. 2 allows load balancing to be performed on the servers of group 20 as normal.

Figure 3:
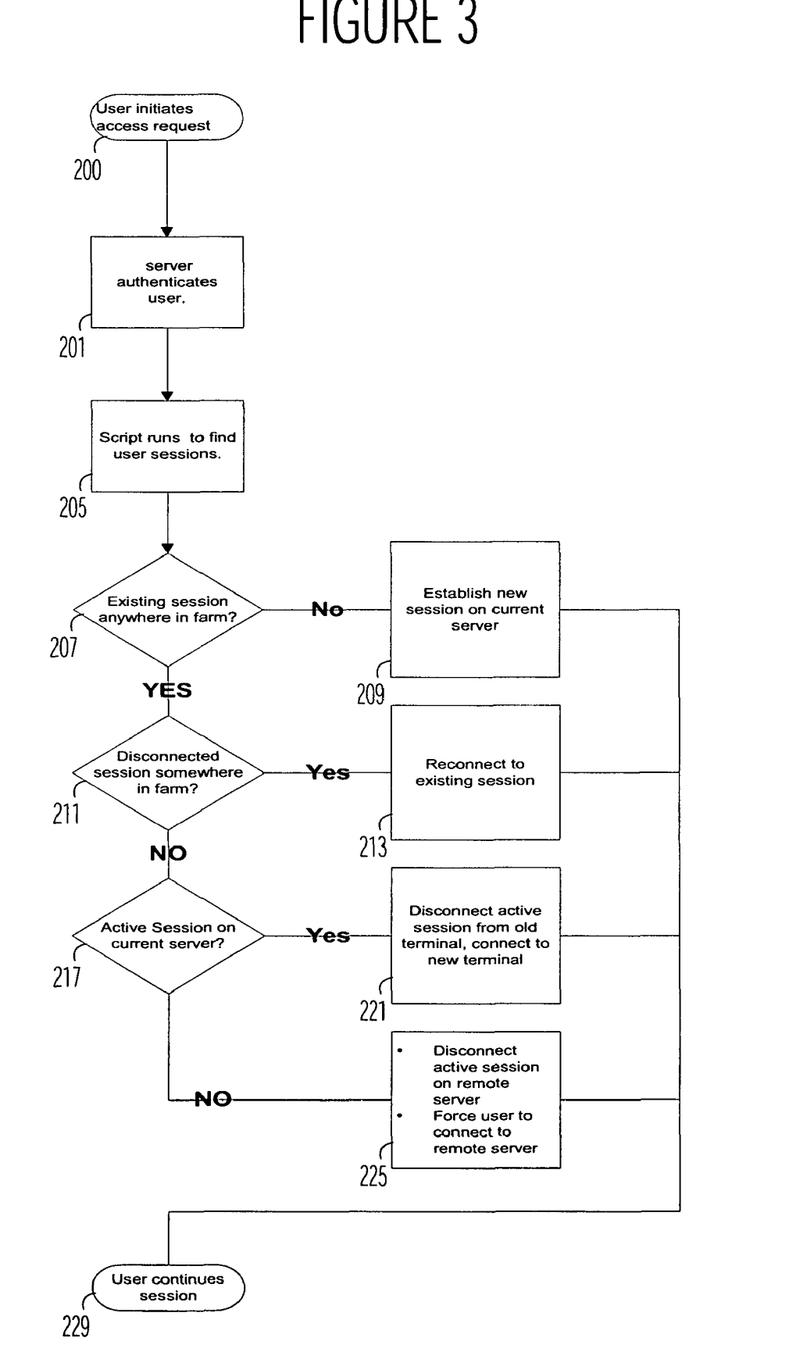
FIG. 3 shows a flowchart of a process used in the system of FIG. 1 for managing user operation sessions on one or more different servers, according to invention principles.

FIG. 3 shows a flowchart of a process used in the system of FIG. 2 for managing user operation sessions on one or more different servers. In response to a user initiating a request to access an application and receiving user identification information in step 200, an authentication procedure (such as a Citrix compatible procedure) executes in step 201 to determine whether the user is authorized to access the requested application. In step 205, the application 17 script procedure executes to interrogate servers of group 20 to determine if the user has any other existing sessions in server group 20. If the application 17 script procedure determines in step 207 that there are no other sessions anywhere in server group 20 for this user, a new session of operation is created on the current server and the user continues with the created session in step 229. If the application 17 script procedure determines in step 207 that there is at least one other session for this user on a server in server group 20, the script procedure determines in step 211 whether there is a disconnected session for this user on a server in server group 20. In response to detection of a disconnected session in step 211, the application 17 script procedure in step 213 re-attaches connection to the disconnected session and the user continues with this session in step 229.

If the application 17 script procedure determines in step 211 that there is no disconnected session for this user on a server in server group 20, the script procedure determines in step 217 whether there is an active session for this user on a current server (of server group 20) to which a user workstation is connected. A current server is a server to which a workstation currently employed by a user is connected. In response to detection in step 217 of an active session on a current server (of server group 20) to which a previously employed user workstation is connected, the application 17 script procedure in step 221 detaches the connection between the active session on the current server and the previously employed workstation to which it is connected. The application 17 script procedure re-attaches connection of a workstation currently employed by the user to the now disconnected active session on the current server and the user continues with this session in step 229. In response to no active session being detected on a current server (of server group 20) in step 217, the application 17 script procedure in step 225 detaches a connection between an active session on a remote (non-current) server and a workstation previously employed by the user to which the session is connected. The application 17 script procedure re-attaches connection of a workstation currently employed by the user to the now disconnected active session on the remote server and the user continues with this session in step 229.

Figure 4:
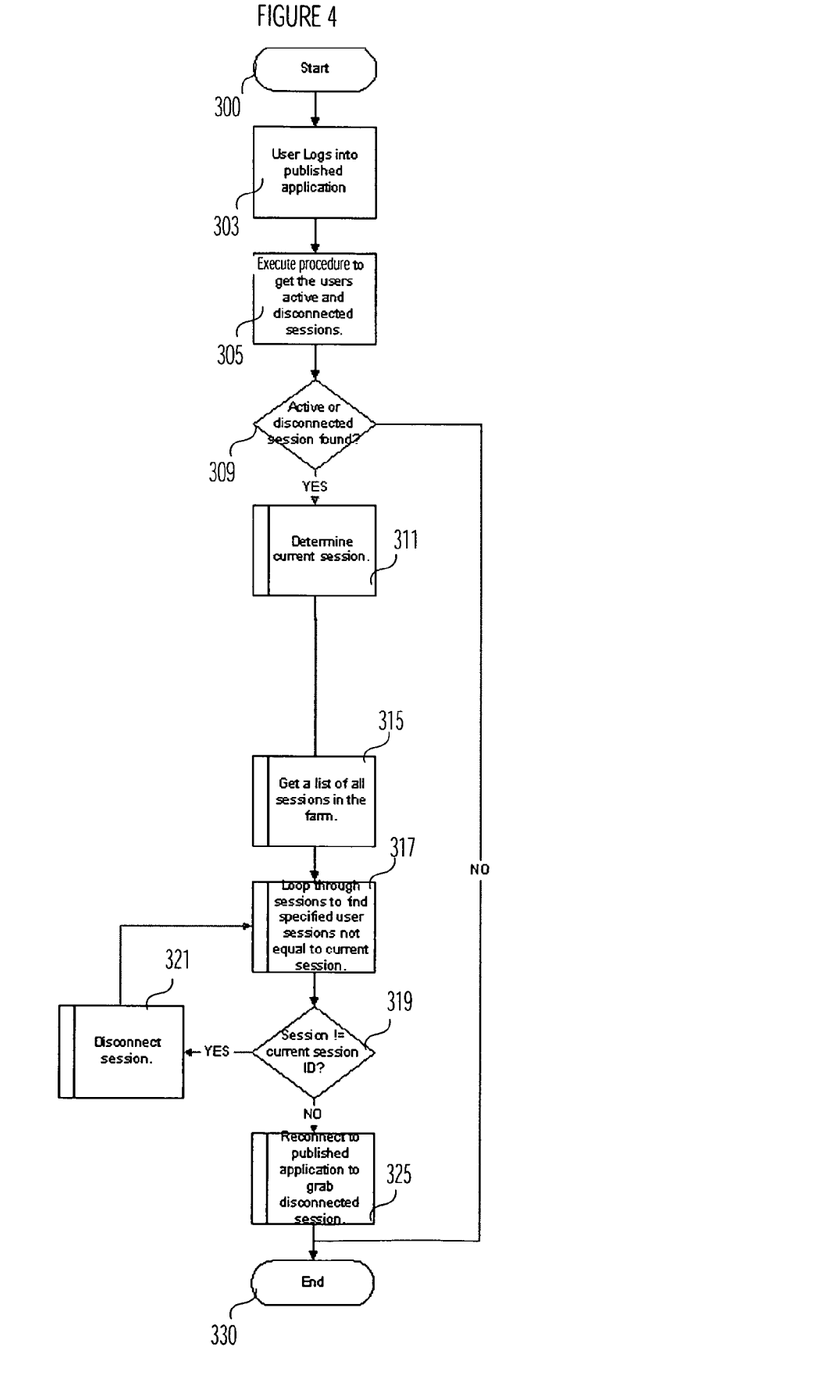
FIG. 4 shows a flowchart of a process used to identify and re-connect to previous user operation sessions, according to invention principles.

FIG. 4 shows a flowchart of a process used in the system of FIG. 2 to identify and re-connect to previous user operation sessions. A user logs on to an executable application such as application 30 (FIG. 2) in step 303, following the start at step 300. In step 305 in response to user logon, a script procedure such as the application 17 script procedure executes to identify active and disconnected sessions of operation of the user present on servers in server group 20. If the application 17 script procedure determines in step 309 that there are no active or disconnected sessions of operation of the user present on servers in server group 20, the process terminates at step 330. If the application 17 script procedure determines in step 309 that there are active or disconnected sessions of operation of the user present on servers in server group 20, the application 17 script procedure obtains a session identifier of a current session of operation of an application in step 311. The current session is hosted by a current server to which a workstation currently employed by a user is connected.

The application 17 script procedure in step 315 obtains data identifying the sessions of operation present on the servers of group 20. In steps 317, 319 and 321 the application 17 script procedure disconnects the sessions identified in step 315 having session identifiers different to the session identifier of the current session previously obtained in step 311. The sessions disconnected in steps 317, 319 and 321 are disconnected without user performance of a workstation logout function. The application 17 script procedure in step 325 re-attaches the connection of a session of operation disconnected in step 321 to the current user workstation in response to user logon in step 303. The process of FIG. 4 terminates at step 330.

Figure 5:
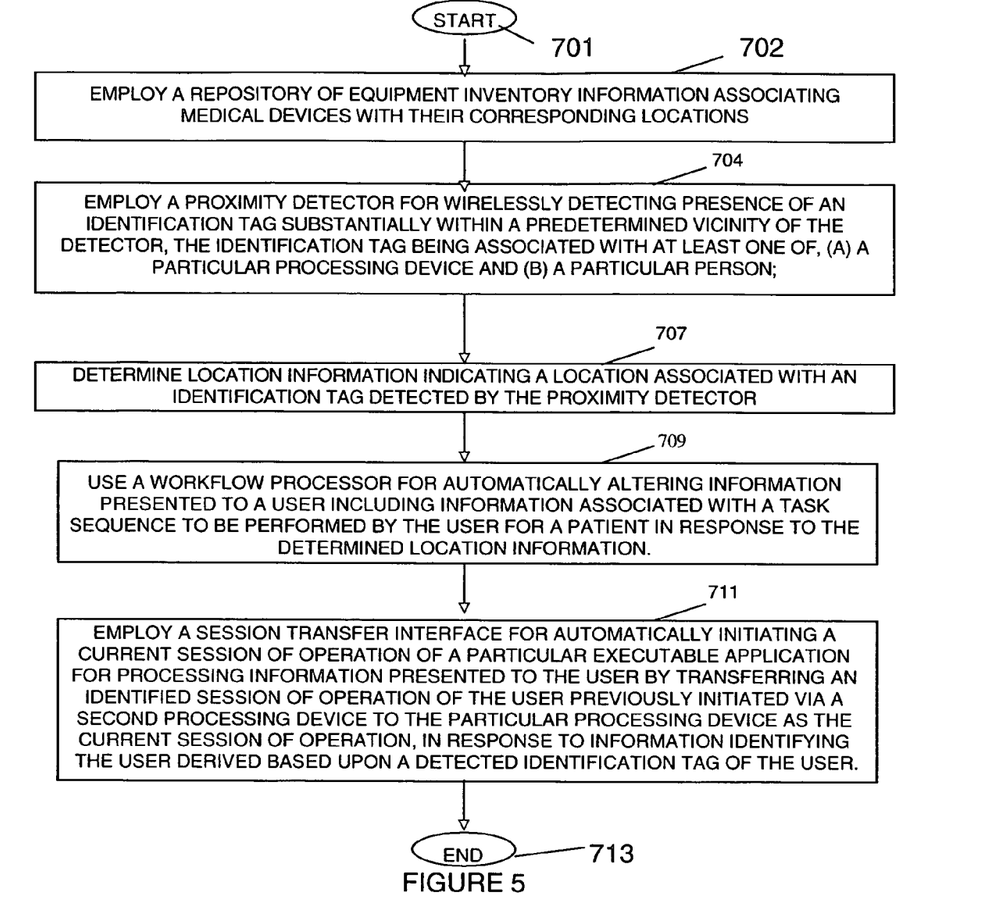
FIG. 5 shows a flowchart of a process used for determining changes in information presented in user interface workflows, screens, menus, and access requirements for devices provided to a user in response to received location dependent context data, according to invention principles.

FIG. 5 shows a flowchart of a process used for determining changes in information presented in user interface workflows, screens, menus, and access requirements for devices provided to a user in response to received location dependent context data. In step 702 following the start at step 701 system 100 stores equipment inventory information in repository 127 associating medical devices, comprising patient parameter acquisition devices, with their corresponding locations and with individual patients and with patient care units (rooms). In step 704, proximity detector 123 wirelessly detects presence of an identification tag substantially within a predetermined vicinity of the detector. The identification tag is associated with a particular processing device or a particular person (the particular person is a particular healthcare worker or a particular patient) and is an RFID tag and proximity detector 123 comprises an RFID processor for detecting an RFID tag, for example. In another embodiment the identification tag and proximity detector 123 employs Global Positioning technology, IEEE 802 compatible technology or infra-red technology. A location detector in application 121 in step 707 determines location information indicating a location associated with an identification tag detected by proximity detector 123.

In step 709 a workflow processor in application 121 (or in another embodiment in HIS application 125) automatically alters information presented to a user including information associated with a task sequence to be performed by the user for a patient in response to the determined location information. The workflow processor alters information presented to the user including information associated with a task sequence to be performed by the user in response to information identifying a role performed by the user or information identifying a patient. Similarly, the workflow processor alters information presented to the user (e.g., on a particular portable processing device used by a healthcare worker) to include information derived from particular medical devices in a vicinity of the determined location in response to information identifying a patient. The identified role information and patient identification information is derived based upon a detected identification tag of the user and the role performed by the user comprises a physician role, a nurse role, an administrative role or a clinician role. The workflow processor uses the equipment inventory information in automatically altering information presented to the user to include information derived from particular medical devices in a vicinity of the determined location and to exclude information from devices not in a vicinity of the determined location. The vicinity of the determined location comprises a patient care unit, for example.

In step 711, a session transfer interface in application 121 automatically initiates a current session of operation of a particular executable application for processing information presented to the user by transferring an identified session of operation of the user previously initiated via a second processing device. Application 121 transfers the identified session (an active session) of operation of the user to the particular processing device as the current session of operation, in response to information identifying the user derived based upon a detected identification tag of the user. The session transfer interface initiates, identifying the session of operation of the user previously initiated via the second processing device, and re-attaching connection of the previously initiated session of operation to the first processing device as the current session of operation. The process of FIG. 5 terminates at step 713.

The systems and processes presented in FIGS. 1-5 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system according to invention principles is usable wherever mobile personnel, devices and resources are tracked to automatically establish context information determining changes to user interface workflows, screens, menus, and access requirements for devices. Further, any of the functions provided systems and processes of FIGS. 1-5 may be implemented in hardware, software or a combination of both and may reside on one or more processing devices located at any location of a network linking the FIG. 1 or 2 elements or another linked network including another intra-net or the Internet.

What is claimed is:

1. A healthcare system for determining information provided to a healthcare worker in response to received location dependent context data, comprising:
   a proximity detector for wirelessly detecting presence of an identification tag attached to a healthcare worker substantially within a predetermined vicinity of said detector;
   a location detector for determining location information indicating a location associated with an identification tag attached to said healthcare worker detected by said proximity detector and for identifying at least one patient associated with said healthcare worker in the vicinity of the determined location from predetermined information associating patients with geographic location;
   a workflow processor for automatically adaptively selecting tasks to be performed by said healthcare worker associated with the identified at least one patient and presenting information to said healthcare worker identifying the selected tasks in a task sequence to be performed by said healthcare worker for the identified at least one patient in response to the detection of said identification tag attached to said healthcare worker; and
   a user interface for automatically presenting display images including medical information of the identified at least one patient in response to the detection of said identification tag attached to said healthcare worker.

2. A system according to claim 1, wherein
   said location detector identifies medical equipment in the vicinity of the determined location from predetermined information associating equipment with geographic location,
   said user interface automatically presents display images including medical information of the identified at least one patient acquired from the identified medical equipment and laboratory test results of the identified at least one patient in response to the detection of said identification tag attached to said healthcare worker,
   said identification tag is an RFID tag and
   said proximity detector comprises an RFID processor for detecting an RFID tag.

3. A system according to claim 1, wherein
said location detector identifies medical equipment in the vicinity of the determined location from predetermined information associating equipment with geographic location,
said user interface automatically presents display images including medical information of the identified at least one patient acquired from the identified medical equipment in response to the detection of said identification tag attached to said healthcare worker and
said identification tag and proximity detector employs at least one of, (a) RFID technology, (b) Global Positioning technology, (c) IEEE 802 compatible technology and (d) infra-red technology.

4. A system according to claim 1, wherein
said workflow processor alters information presented to said healthcare worker by adapting a workflow, display images and access requirements of devices accessible by said healthcare worker and by including information associated with a task sequence to be performed for the at least one identified patient by said healthcare worker in response to information identifying a role performed by said healthcare worker, said identified role information being derived based upon a detected identification tag attached to said healthcare worker.

5. A system according to claim 4, wherein
said role performed by said healthcare worker comprises at least one of, (a) a physician role, (b) a nurse role, (c) an administrative role and (d) a clinician role.

6. A system according to claim 1, wherein
said workflow processor alters information presented to said healthcare worker including information associated with a task sequence to be performed by said healthcare worker in response to information identifying a patient, said patient identification information being derived based upon a detected identification tag of said patient.

7. A system according to claim 1, including
a repository of equipment inventory information associating medical devices with their corresponding locations wherein
said workflow processor uses said equipment inventory information in automatically altering information presented to said healthcare worker to include information derived from particular medical devices in a vicinity of said determined location and to exclude information from devices not in a vicinity of said determined location.

8. A system according to claim 7, wherein
said particular medical devices comprise patient parameter acquisition devices.

9. A system according to claim 8, wherein
said workflow processor alters information presented to said healthcare worker to include information derived from particular medical devices in a vicinity of said determined location in response to information identifying a patient, said patient identification information being derived based upon a detected identification tag of said patient.

10. A system according to claim 9, wherein
said vicinity of said determined location comprises a patient care unit.

11. A system according to claim 1, wherein
said information presented to said healthcare worker is presented on a particular processing device and including
a session transfer interface for automatically initiating a current session of operation of a particular executable application for processing information presented to said healthcare worker by transferring an identified session of operation of said healthcare worker previously initiated via a second processing device to said particular processing device as said current session of operation, in response to information identifying said healthcare worker derived based upon a detected identification tag of said healthcare worker.

12. A system according to claim 11, wherein
said identified session of operation is an active session.

13. A system according to claim 12, wherein
said session transfer interfaces initiates,
identifying said session of operation of said healthcare worker previously initiated via said second processing device, and
re-attaching connection of said previously initiated session of operation to said first processing device as said current session of operation.

14. A system according to claim 1, wherein
said particular processing device is a portable processing device used by a healthcare worker and
said particular person is a particular healthcare worker.

15. A system according to claim 14, wherein
said particular person is a particular patient.

16. A healthcare system for selecting information to be provided to a healthcare worker in response to received location dependent context data comprising:
a proximity detector for wirelessly detecting presence of an identification tag of a particular processing device substantially within a predetermined vicinity of said detector, said processing device being associated with a healthcare worker;
a location detector for determining location information indicating a location associated with said identification tag associated with said healthcare worker detected by said proximity detector and for identifying at least one patient associated with said healthcare worker in the vicinity of the determined location from predetermined information associating patients with geographic location;
a workflow processor for automatically adaptively selecting tasks to be performed by said healthcare worker associated with the identified at least one patient and selecting information presented to said healthcare worker identifying the selected tasks in a task sequence to be performed by said healthcare worker for the identified at least one patient in response to the detection of said identification tag attached, said information being presented to said healthcare worker using said particular processing device; and
a user interface for automatically presenting display images including medical information of the identified at least one patient in response to the detection of said identification tag.

17. A system according to claim 16, including
a repository of equipment inventory information associating medical devices with their corresponding locations wherein
said location detector identifies medical equipment in the vicinity of the determined location from the equipment inventory information,
said user interface automatically presents display images including medical information of the identified at least one patient acquired from the identified medical equipment and laboratory test results of the identified at least one patient in response to the detection of said identification tag, said workflow processor uses said equipment inventory information in automatically altering information presented to said healthcare worker to include information derived from particular medical devices in a vicinity of said determined location and to exclude information from devices not in a vicinity of said determined location.

18. A system according to claim 17, wherein
said equipment inventory information associates medical devices with individual patients and with patient care units (rooms).

19. A system according to claim 17, wherein
said workflow processor selects information presented to said healthcare worker to include information derived from particular medical devices in a vicinity of said determined location in response to information identifying a patient, said patient identification information being derived based upon a detected identification tag of said patient.

20. A system according to claim 16, including
a session transfer interface for automatically initiating a current session of operation of a particular executable application for processing information presented to said healthcare worker by transferring an identified session of operation of said healthcare worker previously initiated via a second processing device to said particular processing device as said current session of operation, in response to information identifying said healthcare worker derived based upon a detected identification tag of said healthcare worker.

21. A system according to claim 16, including
a repository of patient location information associating patients with their corresponding care units wherein
said workflow processor uses said patient location information to select information presented to said healthcare worker to include information derived from particular medical devices in a vicinity of said determined location in a particular care unit, said patient location information being derived based upon a detected identification tag of said patient.

22. A healthcare system for determining information to be provided to a healthcare worker in response to received location dependent context data, comprising:
a proximity detector for wirelessly detecting presence of an identification tag attached to a healthcare worker substantially within a predetermined vicinity of said detector and for wirelessly detecting presence of an identification tag of a particular patient substantially within a predetermined vicinity of said detector;
a location detector for determining location information indicating a location associated with an identification tag attached to said healthcare worker detected by said proximity detector and for identifying at least one patient associated with said healthcare worker in the vicinity of the determined location from predetermined information associating patients with geographic location and for determining location information indicating a location associated with said identification tag of said particular patient detected by said proximity detector; and
a workflow processor for automatically adaptively selecting tasks to be performed by said healthcare worker associated with the identified at least one patient and presenting information to said healthcare worker identifying the selected tasks in a task sequence to be performed by said healthcare worker for the identified at least one patient and a task sequence for said particular patient in response to the detection of said identification tag attached to said healthcare worker; and
a user interface for automatically presenting display images including medical information of the identified at least one patient in response to the detection of said identification tag attached to said healthcare worker.

23. A system according to claim 22, wherein
said workflow processor selects information presented to said healthcare worker in response to information identifying a role performed by said healthcare worker, said identified role information being derived based upon a detected identification tag of said healthcare worker wherein
said role performed by said healthcare worker comprises at least one of, (a) a physician role, (b) a nurse role and (c) a clinician role.

24. A system according to claim 22, including
a repository of equipment inventory information associating medical devices with their corresponding locations wherein
said workflow processor uses said equipment inventory information in automatically altering information presented to said healthcare worker to include information derived from particular medical devices in a vicinity of said determined location and to exclude information from devices not in a vicinity of said determined location.

25. A system according to claim 22, wherein
said workflow processor selects information presented to said healthcare worker to include information derived from particular medical devices in a vicinity of said determined location in response to said detected identification tag of said particular patient.

26. A system according to claim 22, including
a session transfer interface for automatically initiating a current session of operation of a particular executable application for processing information presented to said healthcare worker by transferring an identified session of operation of said healthcare worker previously initiated via a second processing device to said particular processing device as said current session of operation, in response to information identifying said healthcare worker derived based upon a detected identification tag of said healthcare worker.

27. A healthcare system for selecting information to be provided to a healthcare worker in response to received location dependent context data, comprising:
a proximity detector for wirelessly detecting presence of an identification tag of a particular healthcare worker substantially within a predetermined vicinity of said detector;
a location detector for determining location information indicating a location associated with said identification tag of said healthcare worker detected by said proximity detector and for identifying at least one patient associated with said healthcare worker in the vicinity of the determined location from predetermined information associating patients with geographic location and for identifying medical equipment in the vicinity of the determined location from predetermined information associating equipment with geographic location; and
a workflow processor for automatically selecting medical information of the identified at least one patient acquired from the identified medical equipment and presented to a healthcare worker including information associated with a task sequence to be performed by said healthcare worker for the identified at least one patient in response to said the detection of said identification tag of said healthcare worker.

28. A system according to claim 27, wherein said workflow processor selects information presented to said healthcare worker in response to information identifying a role performed by said healthcare worker, said identified role information being derived based upon a detected identification tag of said healthcare worker wherein said role performed by said healthcare worker comprises at least one of, (a) a physician role, (b) a nurse role, (c) an administrative role and (d) a clinician role and including a user interface for automatically presenting display images including medical information of the identified at least one patient in response to the detection of said identification tag.

29. A system according to claim 27, including a repository of equipment inventory information associating medical devices with their corresponding locations wherein said workflow processor uses said equipment inventory information in automatically altering information presented to said healthcare worker to include information derived from particular medical devices in a vicinity of said determined location and to exclude information from devices not in a vicinity of said determined location.

30. A system according to claim 27, wherein said workflow processor selects information presented to said healthcare worker to include information derived from particular medical devices in a vicinity of said determined location in response to said detected identification tag of said particular patient.

31. A system according to claim 27, including a session transfer interface for automatically initiating a current session of operation of a particular executable application for processing information presented to said healthcare worker by transferring an identified session of operation of said healthcare worker previously initiated via a second processing device to said particular processing device as said current session of operation, in response to detection of said identification tag of said healthcare worker.

32. A system according to claim 24, wherein said equipment inventory information associates medical devices with individual patients and with patient care units (rooms).

33. A system according to claim 29, wherein said equipment inventory information associates medical devices with individual patients and with patient care units (rooms).

* * * * *